(12) United States Patent
Lee

(10) Patent No.: US 7,833,193 B2
(45) Date of Patent: Nov. 16, 2010

(54) CATHETER SHAFT JUNCTION HAVING A POLYMERIC MULTILAYERED SLEEVE WITH A LOW PROCESSING TEMPERATURE OUTER LAYER

(75) Inventor: Jeong S. Lee, Diamond, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/687,265

(22) Filed: Jan. 14, 2010

(65) Prior Publication Data

US 2010/0122768 A1 May 20, 2010

Related U.S. Application Data

(60) Division of application No. 11/196,134, filed on Aug. 2, 2005, now Pat. No. 7,662,130, which is a continuation-in-part of application No. 10/010,212, filed on Dec. 4, 2001, now Pat. No. 7,037,291.

(51) Int. Cl.
*A61M 29/00* (2006.01)
(52) U.S. Cl. .............................. 604/103.04; 604/96.01
(58) Field of Classification Search .............. 604/96.01, 604/103–103.14, 523–527
See application file for complete search history.

(56) References Cited

U.S. PATENT DOCUMENTS

| | | | |
|---|---|---|---|
| 5,155,835 A | 10/1992 | Belsan | |
| 5,156,594 A | 10/1992 | Keith | |
| 5,390,313 A | 2/1995 | Yanai et al. | |
| 5,403,639 A | 4/1995 | Belsan et al. | |
| 5,430,855 A | 7/1995 | Walsh et al. | |
| 5,620,649 A | 4/1997 | Trotta | |
| 5,689,481 A | 11/1997 | Tamura et al. | |
| 5,819,310 A | 10/1998 | Vishiltzky et al. | |
| 5,835,939 A | 11/1998 | Kurokawa et al. | |
| 5,897,661 A | 4/1999 | Baranovsky et al. | |
| 6,024,722 A | 2/2000 | Rau et al. | |
| 6,105,118 A | 8/2000 | Maddalozzo et al. | |
| 6,193,686 B1 | 2/2001 | Estrada et al. | |
| 6,292,626 B1 | 9/2001 | Ino et al. | |
| 6,321,239 B1 | 11/2001 | Shackelford | |
| 6,360,232 B1 | 3/2002 | Brewer et al. | |
| 6,400,657 B1 | 6/2002 | Soeda et al. | |
| 6,404,707 B1 | 6/2002 | Kaneda et al. | |
| 6,577,562 B2 | 6/2003 | Gallo et al. | |
| 6,643,667 B1 | 11/2003 | Arai et al. | |
| 6,662,197 B1 | 12/2003 | LeCrone et al. | |
| 6,733,487 B2 | 5/2004 | Keith et al. | |
| 6,792,503 B2 | 9/2004 | Yagi et al. | |
| 6,880,058 B2 | 4/2005 | Mizuno et al. | |

FOREIGN PATENT DOCUMENTS

| | | |
|---|---|---|
| EP | 0931558 | 7/1999 |
| JP | 2000-137639 | 5/2000 |
| JP | 2001-092703 | 4/2001 |

*Primary Examiner*—Matthew F Desanto
(74) *Attorney, Agent, or Firm*—Fulwider Patton LLP

(57) ABSTRACT

One aspect of the invention is directed to a balloon catheter with a multilayered polymeric sleeve at the rapid exchange intermediate section, having an outer layer formed of a polymer with a relatively low processing temperature (i.e., melting temperature for semi-crystalline polymers or glass transition temperature for amorphous polymers), and having an inner layer.

1 Claim, 7 Drawing Sheets

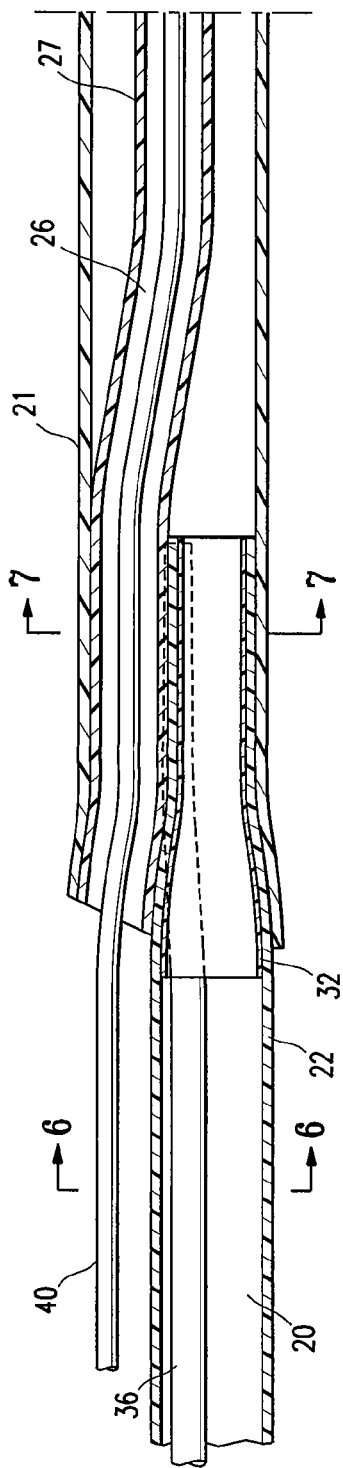
FIG. 5
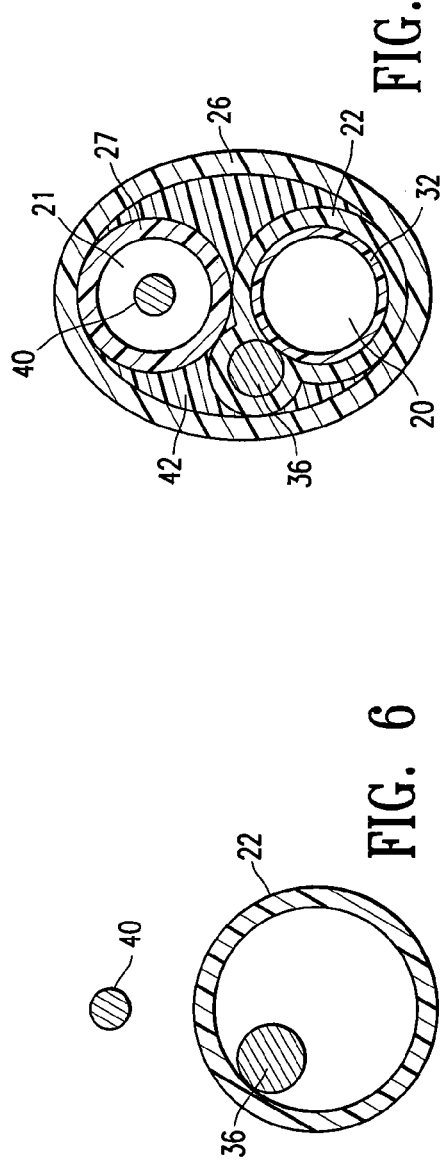
FIG. 7
FIG. 6

CATHETER SHAFT JUNCTION HAVING A POLYMERIC MULTILAYERED SLEEVE WITH A LOW PROCESSING TEMPERATURE OUTER LAYER

CROSS-REFERENCES TO RELATED APPLICATIONS

This is a divisional application of U.S. Ser. No. 11/196,134, filed on Aug. 2, 2005; which is a continuation-in-part of U.S. Ser. No. 10/101,212, filed on Mar. 20, 2002, issued on Dec. 11, 2007, U.S. Pat. No. 7,308,533. Applicant claims priority to each application in the chain. Each of the foregoing applications is incorporated by reference herein in its entirety.

BACKGROUND OF THE INVENTION

This invention relates generally to catheters, and particularly to intravascular catheters for use in percutaneous transluminal coronary angioplasty (PTCA), or the delivery of stents.

In a typical PTCA procedure, a dilatation balloon catheter is advanced over a guidewire to a desired location within the patient's coronary anatomy to position the balloon of the dilatation catheter along the stenosis to be dilated. The balloon is then inflated one or more times with fluid at relatively high pressures (generally 4-16 atmospheres) to dilate the stenosed region of the diseased artery. A stent is commonly implanted within the artery, typically by delivery to the desired location within the artery in a contracted condition on a balloon of a catheter which is similar in many respects to a balloon angioplasty catheter. Inflation of the balloon expands the stent, thereby implanting it in the artery. Following the dilatation or stent expansion, the balloon is deflated and the catheter repositioned or withdrawn from the artery.

In rapid exchange type balloon catheters, the catheter has an inflation lumen extending from the proximal end of the catheter to a balloon on a distal shaft section, a distal guidewire port at the distal end of the catheter, a proximal guidewire port located distal to the proximal end of the catheter, and a relatively short guidewire lumen extending therebetween. The rapid exchange junction located at the proximal guidewire port should provide a good transition in flexibility from the relatively stiff proximal shaft section to the relatively flexible distal shaft section. One difficulty has been forming a junction which is flexible, yet kink resistant and rugged.

To help meet the desire for a catheter having sufficient pushability and crossability, while maintaining trackability within the patient's tortuous vasculature, prior art designs have supplemented polymer catheter shafts with a support mandrel. Other prior art designs have addressed these handling and performance issues by using materials of different stiffness for the proximal and distal portions of the catheter, and employing a high strength metallic proximal shaft section, commonly called a hypotube. To prevent kinking at the junction of these two materials, while maintaining trackability, some conventional designs have employed reinforcing layers or stiffening wires to bridge the transition in catheter shaft material. Despite these attempts, prior art designs have suffered from various drawbacks relating to these handling and performance issues.

Accordingly, it would be a significant advance to provide a catheter having an improved catheter shaft junction between shaft sections such as the proximal and distal shaft sections. This invention satisfies these and other needs.

SUMMARY OF THE INVENTION

The invention is generally directed to a balloon catheter having a polymeric reinforcing member or multilayered sleeve at a junction between shaft sections such as the junction between the proximal shaft section and the distal shaft section. In a presently preferred embodiment, the balloon catheter is a rapid exchange type catheter. The polymeric reinforcing member is around or within either or both of the tubular member defining the inflation lumen or the tubular member defining the guidewire lumen at the rapid exchange junction. In another embodiment, the balloon catheter has a multilayered polymeric sleeve at the rapid exchange intermediate section, having an outer layer formed of a polymer having a relatively low glass transition temperature or melting temperature, and an inner layer. The reinforcing tubular member or the multilayered polymeric sleeve at the rapid exchange junction of the shaft prevents or inhibits damage to the tubular members defining the inflation lumen and/or guidewire lumen during assembly or use of the catheter, and thus avoids a loss of lumen integrity.

The balloon catheter of the invention generally comprises an elongated shaft having a proximal shaft section, a distal shaft section, an inflation lumen, a guidewire receiving lumen extending within at least the distal shaft section, and a balloon on the distal shaft section with an interior in fluid communication with the inflation lumen. The shaft proximal shaft section comprises a proximal tubular member having a proximal end, a distal end, a distal portion, and defining a proximal portion of the inflation lumen. The shaft distal shaft section comprises an outer tubular member and an inner tubular member within the outer tubular member lumen. The outer tubular member defines a distal portion of the inflation lumen, and the inner tubular member defines the guidewire receiving lumen in fluid communication with a guidewire distal port at the distal end of the catheter shaft, and a guidewire proximal port at the proximal end of the inner tubular member. As a rapid exchange type catheter, the proximal guidewire port at the rapid exchange junction is located at the proximal end of the distal shaft section, distal to the proximal end of the catheter shaft. The inner tubular member has a proximal portion generally in a side-by-side relationship with the distal portion of the proximal tubular member. The polymeric reinforcing member is located around or within the proximal portion of the inner tubular member or the distal portion of the proximal tubular member.

The polymeric reinforcing member is preferably a tube having a shape configured to correspond to the shape of the proximal portion of the inner tubular member or the distal portion of the proximal tubular member, such as a circular, oblong/oval, D-shaped or C-shaped transverse cross section. However, a variety of suitable shapes may be used depending on the shape of the inner tubular member and the proximal tubular member. In a presently preferred embodiment, the polymeric reinforcing member is formed of a first polymeric material having a glass transition temperature greater than a glass transition temperature of a second polymeric material forming the distal portion of the proximal tubular member or the proximal portion of the inner tubular member. The first polymeric material forming the polymeric reinforcing member is preferably a high temperature, high modulus material, having a glass transition temperature (Tg) of about 300° C. to about 450° C., and a tensile modulus, expressed as a secant modulus (ASTM D882) of about 350,000 to about 450,000 psi. In one embodiment, the first polymeric material forming the polymeric reinforcing member is selected from the group consisting of thermoset polyimide and thermoplastic polyimide. The thermoset or thermoplastic polyimide has a high secant modulus of greater than about 350,000 psi, with about 25,000 to about 30,000 psi tensile strength, which allows for a thin-walled reinforcing tube which nonetheless has a sufficient strength to provide the required reinforcement. In a presently preferred embodiment, thermoset polyimide is used, due to the high glass transition temperature of the thermoset polyimide. The thermoset polyimide has a very high glass transition temperature (Tg) of approximately 400° C. (as measured by differential scanning calorimetry (DSC)), and thus excellent dimensional stability at the processing temperature of other polymers such as polyamides and polyurethanes commonly used in catheter components. As a result, the polyimide tube maintains thin-walled, controlled dimensions during formation and assembly of the catheter, and specifically during high temperature fusion (i.e., thermal) bonding of the tubular members to form the rapid exchange junction. Thermoplastic polyimide, which has a Tg of about 250° C., may also be used, but is less preferred than the high glass transition temperature thermoset polyimide.

In one embodiment, the second polymeric material forming the distal portion of the proximal tubular member or the proximal portion of the inner tubular member is selected from the group consisting of polyether block amide (PEBAX), nylon, and polyurethane, although a variety of suitable polymeric materials different from the first polymeric material and useful in the formation of catheter shafts can be used. The glass transition temperature of the second polymeric material forming the distal portion of the proximal tubular member or the proximal portion of the inner tubular member is typically about 30° C. to about 60° C., and more specifically about 35° C. to about 55° C. Similarly, in one embodiment, the polymeric material forming a proximal portion of the outer tubular member is selected from the group consisting of PEBAX, nylon, and polyurethane, although a variety of suitable polymeric materials different from the first polymeric material and useful in the formation of catheter shafts can be used. The distal portion of the proximal tubular member and the proximal portion of the inner tubular member are preferably formed of compatible materials which are fusion bondable together. In one embodiment, adhesive is not used at the rapid exchange junction to bond the distal portion of the proximal tubular member and the proximal portion of the inner tubular member together, which are instead fusion bonded together.

The polymeric reinforcing member has sufficient wall thickness to prevent or inhibit the formation of a break in the wall of the tubular members defining the inflation lumen and the guidewire lumen at the rapid exchange junction. During assembly of the catheter, assembly mandrels or rods (hereafter "assembly rods"), are placed in the lumens of the proximal tubular member and the distal inner tubular member, to keep the lumens open during fusion of the tubular members to form the rapid exchange junction. Heat, and pressure from shrink tubing are applied to the tubular members to fusion bond the tubular members together and form the rapid exchange junction at the transition between the proximal or an intermediate shaft section and the distal shaft section at the guidewire proximal port. The polymeric reinforcing member prevents or inhibits loss of integrity of the inner tubular member and proximal tubular member caused by junction formation as the heated polymeric material of the tubular members are flow together during fusion bonding. Thus, leaks in the guidewire and inflation lumens are prevented or inhibited by the polymeric reinforcing member with a high glass transition temperature.

In one embodiment, a supporting member such as a mandrel is provided within at least a section of the inflation lumen, to enhance the catheter's pushability and crossability. The length and position of the support mandrel within the catheter shaft may vary . Typically, the support mandrel extends distally from the proximal end of the catheter shaft, or from an intermediate location distal to the proximal end of the catheter shaft,. The support mandrel is preferably a solid metal or high modulus polymer material, although a variety of different supporting members can be used including solid or hollow rods, wires, and the like. In the embodiment having the polymeric reinforcing member in the inflation lumen, the support mandrel extends adjacent an inner or outer surface of the polymeric reinforcing member, either in contact with or spaced apart from the surface of the polymeric reinforcing member. In one embodiment the support mandrel is releasably secured (i.e., not fixedly secured) to the shaft, and is thus free to be removed therefrom. In an alternative embodiment, the support mandrel distal section is embedded in polymeric material at or near the rapid exchange junction. The polymeric reinforcing member prevents or inhibits the support mandrel from extending through, and causing a leak in, the tubular members at the rapid exchange junction. In one embodiment, the support mandrel is bonded to the polymeric reinforcing member. In one embodiment, to facilitate bonding the support mandrel to the polymeric reinforcing member, the polymeric reinforcing member is a multilayered tube having a first layer formed of the first polymeric material (e.g., polyimide), and at least a second layer which is an inner or an outer layer and which is formed of a different polymeric material, such as PEBAX, nylon, polyurethane or polyolefin hot melt adhesive such as Primacor (an EAA copolymer), which adheres to metal.

In an alternative embodiment, the balloon catheter has a multilayered polymeric sleeve at the rapid exchange intermediate section, with an outer layer formed of a polymer which has a relatively low processing temperature (i.e., a relatively low glass transition temperature or melting temperature), and an inner layer. The outer layer facilitates forming the rapid exchange junction at much lower temperatures than are likely in the absence of the outer layer, thus preventing or avoiding thinning of the inner layer of the sleeve. The processing temperature is dictated by the glass transition temperature (Tg) for amorphous polymers, and by the melting temperature (Tm) for semi-crystalline polymers. The Tg and Tm values of polymers, as measured by Differential Scanning Calorimetry (DSC)), are commonly known. In one embodiment, the outer layer of the multilayered polymeric sleeve is selected from the group consisting of an adhesive polymer such as PRIMACOR (DSC Tm of about 90-100° C.), a relatively low durometer polyether block amide (PEBAX) having a hardness of less than about Shore D 55 (DSC Tm of about 110-160° C.), nylon 6,3 (DSC Tg of about 150° C.), polyaryl amide (DSC Tg of about 85° C.), nylon 6,12 (DSC Tm of about 145-220° C.), and nylon 12 (DSC Tm of about 170-185° C.), and the inner layer polymer is selected from the group consisting of a relatively high durometer PEBAX (DSC Tm of about 170° C.), and nylons such as nylon 11 (DSC Tm of about 175-195° C.), nylon 6 (DSC Tm of about 190-220° C.), nylon 6,6 (DSC Tm of about 210-270° C.), nylon 6,10 (DSC Tm of about 210-220° C.), nylon 6, 12 (DSC Tm of about 145-220° C.), and nylon 4, 6 (DSC Tm of about 300° C.), polyphthalamide (DSC Tm of about 145-310° C.), and polyamide-imide (DSC Tg of about 280° C.).

The balloon catheter of the invention can be configured for a variety of applications including coronary angioplasty, peripheral dilatation, stent or graft delivery, drug delivery, and the like. A variety of suitable stents can be used with the balloon catheter of invention, which generally comprise expandable tubular members (for details of stent design, see for example U.S. Pat. No. 5,507,768 (Lau et al.) and U.S. Pat. No. 5,458,615 (Klemm et al.), incorporated by reference herein in their entireties).

The catheter of the invention maintains the integrity of the inflation lumen and guidewire lumen throughout assembly and use of the catheter, due to the polymeric reinforcing member or multilayered polymeric sleeve. The thin-walled polymeric reinforcing member has excellent dimension stability providing a rapid exchange junction having a low profile and a suitable stiffness transition between proximal and distal portions of the catheter, to thereby improve handling and performance and minimize kinking. These and other advantages of the invention will become more apparent from the following detailed description and exemplary drawings.

BRIEF DESCRIPTION OF THE DRAWINGS

FIG. 5 is a longitudinal cross section of the rapid exchange junction shown in FIG. 4, after fusing of the tubular members together to form the junction.

FIG. 6 is a transverse cross sectional view of the catheter shown in FIG. 5, taken along lines 6-6.

FIG. 7 is a transverse cross sectional view of the catheter shown in FIG. 5, taken along lines 7-7.

DETAILED DESCRIPTION OF THE INVENTION

Figure 1:
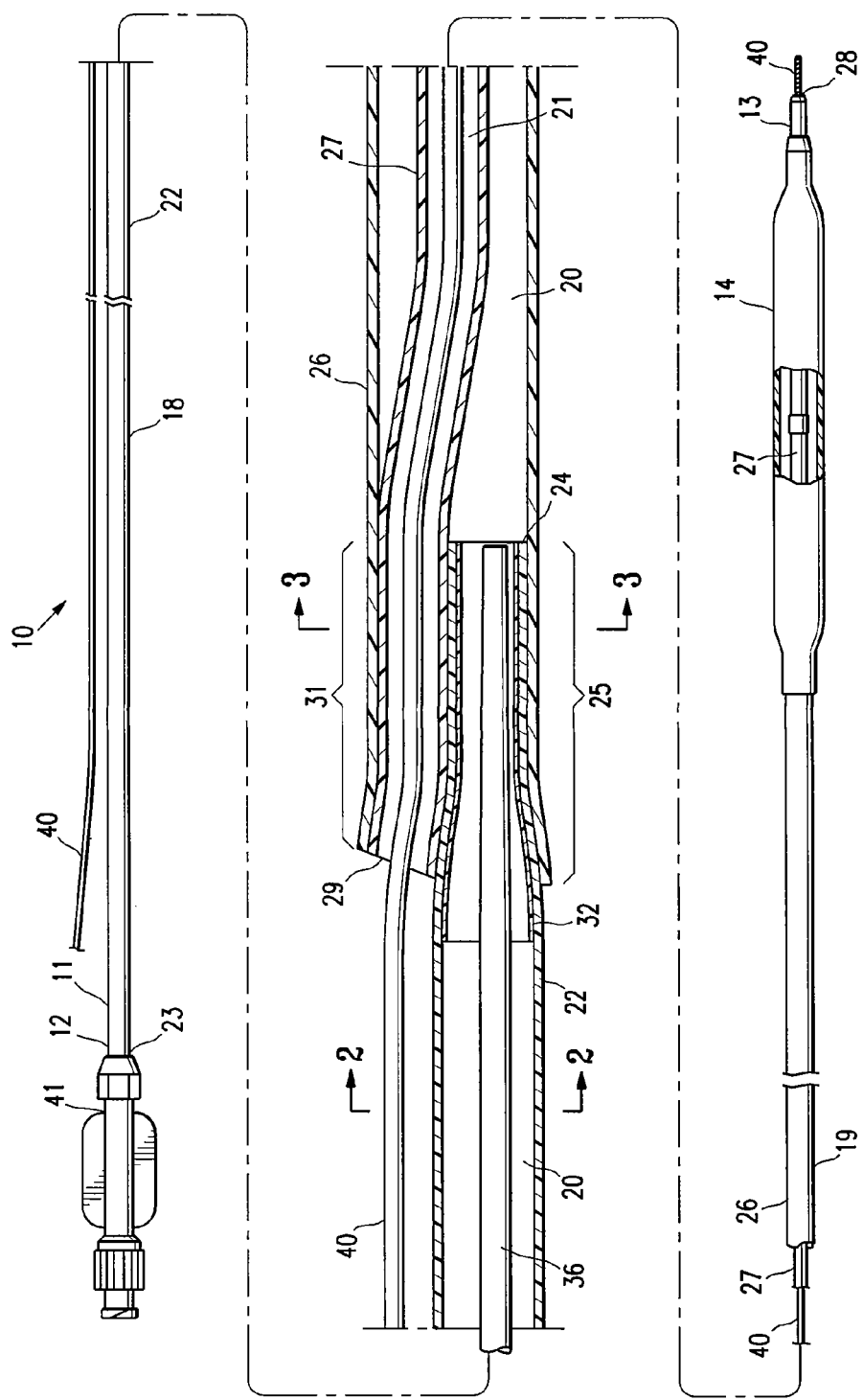
FIG. 1 is an elevational view, partially in section, of a rapid exchange balloon catheter which embodies features of the invention, having a polymeric reinforcing tube in the inflation lumen in the distal end of the proximal tubular member, with a support mandrel having a distal section extending along an inner surface of the polymeric reinforcing tube.
Figure 2:
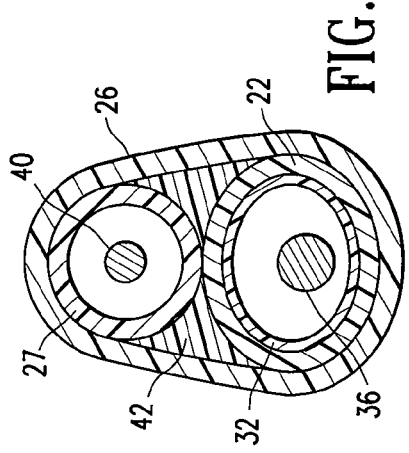
FIG. 2 is a transverse cross sectional view of the catheter shown in FIG. 1, taken along lines 2-2.
Figure 3:
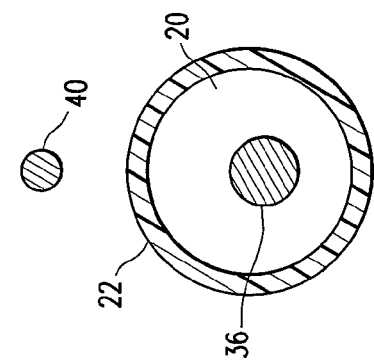
FIG. 3 is a transverse cross sectional view of the catheter shown in FIG. 1, taken along lines 3-3.

FIG. 1 illustrates rapid exchange type balloon catheter 10 embodying features of the invention. Catheter 10 generally comprises an elongated catheter shaft 11 having a proximal end 12, a distal end 13, a proximal shaft section 18 and a distal shaft section 19 at the distal end of the proximal shaft section, and an inflatable balloon 14 on the distal shaft section. The shaft 11 has an inflation lumen 20, and a guidewire receiving lumen 21. The proximal shaft section 18 comprises a proximal tubular member 22 defining a proximal portion of the inflation lumen 20, and having a proximal end 23, a distal end 24, and a distal portion 25. In the embodiment illustrated in FIG. 1, the distal end of the proximal tubular member 22 tapers distally to a smaller transverse dimension. The distal shaft section 19 comprises an outer tubular member 26 defining a distal portion of the inflation lumen 20, and an inner tubular member 27 defining the guidewire lumen 21 in fluid communication with a guidewire distal port 28 at the distal end of the catheter and a guidewire proximal port 29 at the proximal end of the inner tubular member 27, configured to slidably receive guidewire 40 therein. A rapid exchange junction at the guidewire proximal port 29 is the transition between the single lumen proximal shaft section and the multilumen distal shaft section. As best illustrated in FIGS. 2 and 3, showing transverse cross sections of the catheter of FIG. 1, taken along lines 2-2 and 3-3, respectively, the outer tubular member 26 is around and joined to both the inner tubular member 27 and the proximal tubular member 22. Balloon 14 has a proximal end sealingly secured to the distal end of outer tubular member 26 and a distal end sealingly secured to the distal end of inner tubular member 27, so that its interior is in fluid communication with inflation lumen 20. An adapter 41 at the proximal end of the catheter provides access to the inflation lumen 20. The distal end of catheter may be advanced to a desired region of a patient's body lumen in a conventional manner and balloon 14 inflated to perform a procedure such a dilate a stenosis, and catheter 10 withdrawn or repositioned for another procedure.

In the embodiment of FIG. 1, the inner tubular member 27 has a proximal portion 31 in a side-by-side relationship with the distal portion 25 of the proximal tubular member 22. The inner tubular member 27 is joined to an inner surface of the outer tubular member 26 and to an outer surface of the proximal tubular member 22. Distal to the side-by-side portions 25, 31, the inner tubular member 27 transitions to a configuration which is coaxial with the outer tubular member 26, to define a portion of the guidewire lumen 21 surrounded by the inflation lumen 20, in the embodiment of FIG. 1. However, in an alternative embodiment (not shown), all or part of the length of a distal portion of inner tubular member 27 within the inflation lumen 20, located distal to the distal portion 25 of the proximal tubular member 22, is joined to the inner surface of the outer tubular member 26 and is not coaxially located therein. The proximal portion 31 of the inner tubular member 27 is parallel and preferably fusion bonded to the distal portion 25 of the proximal tubular member 22.

In the embodiment of FIG. 1, a polymeric reinforcing member 32 is at least in part within the distal portion 25 of the proximal tubular member 22 on an inner surface thereof. The polymeric reinforcing member 32 extends along the length of the distal portion of the proximal tubular member 22 which is fused to the inner tubular member. In the embodiment of FIG. 1, the polymeric reinforcing member 32 has a proximal end located proximal to the distal portion 25 of the proximal tubular member 22, and a distal end located at the distal end of the proximal tubular member 22. The polymeric reinforcing member 32 is preferably joined to the proximal tubular member 22 by thermal fusion process, and the catheter shaft assembled, according to a method of making a balloon catheter of the invention. Specifically, the polymeric reinforcing member 32 is positioned on an inflation lumen shaping assembly rod (not shown), and positioned within the distal end section of the proximal tubular member 22. It should be understood that the proximal tubular member 22 may be a single tubular member, or alternatively multiple tubes joined end to end, so that the polymeric reinforcing member 32 is positioned within a distal tube of the proximal tubular member 22. For example, in the embodiment in which the proximal portion of the proximal tubular member 22 is formed of a polyetherether ketone (PEEK) tubular member or a metal hypotube, a distal tube such as a polyether block amide (PEBAX) or nylon tubular member is typically bonded to the distal end of the PEEK or hypotube tubular member, and the polymeric reinforcing member 32 placed within the PEBAX or nylon tubular member. The thus combined assembly rod, polymeric reinforcing member 32, and proximal tubular member 22 are then placed in part within the outer tubular member 26 and aligned with the inner tubular member 27, to be radially adjacent to the guidewire proximal port 29 area. An assembly rod (not shown) is positioned in the inner tubular member 27, and the thus assembled rapid exchange junction heated with shrink tubing (not shown) therearound to shrink the shrink tubing and form the thermally fused junction. The shrink tubing and assembly rods are removed, and a reinforcing mandrel 36 is inserted. Due to the high glass transition temperature of the polymeric reinforcing member 32, the integrity of the inflation lumen 20 is maintained. The polymeric reinforcing member 32 of FIG. 1 typically has a length of about 2 to about 10 cm, preferably about 5 cm, an outer diameter of about 0.46 to about 0.83 mm, an inner diameter of about 0.45 to about 0.8 mm, and a wall thickness of about 0.01 to about 0.03 mm.

The polymeric reinforcing member 32 is formed of a first polymeric material having a glass transition temperature greater than a glass transition temperature of a second polymeric material forming the distal portion of the proximal tubular member 22 or the proximal portion of the inner tubular member 27. In a presently preferred embodiment, the second polymeric material forming the distal portion of the proximal tubular member 22 or the proximal portion of the inner tubular member 27 is nylon or a copolyamide such as PEBAX. In a presently preferred embodiment, the first polymeric material is thermoset polyimide. A polyimide reinforcing member 32 is typically formed by a solution process, such as by dip coating a mandrel and removing the mandrel, to thereby produce a tubular member. In a suitable solution forming process, a polyimide solution is dip, or otherwise, coated onto a neckable mandrel, as described in U.S. Pat. Nos. 4,826,706 and 4,659,622, and the Manufacturing Process section of the Phelps Dodge High Performance Conductors brochure, A Primer on Polyimide Tubing, pp. 1, incorporated herein by reference in their entireties, and then separated intact from the mandrel, to thereby produce a tubular member. The dip coated mandrel can be passed through dies to control the outer dimension of the polyimide reinforcing member 32, and the diameter of the removable mandrel determines the inner diameter of the polyimide reinforcing member 32.

In a presently preferred embodiment, the polymeric reinforcing member 32 is a solid-walled tube. In one embodiment, the polymeric reinforcing member 32 consists of a polyimide tube. However, in alternative embodiments, the polymeric reinforcing member 32 is a multilayered tube having a first inner or outer layer formed of the first polymeric material (e.g., polyimide), and a second layer on a surface of the first layer, the second layer being formed of a third polymeric material (not shown). In a presently preferred embodiment, the third polymeric material is the same polymer family as, and compatible with, the second polymeric material forming the distal end of the proximal tubular member 22. The third polymeric material is typically a polyamide such as nylon or PEBAX, or an adhesive polymer such as the ethylene based adhesive PRIMACOR, providing improved bonding of the polymeric reinforcing member 32 to the proximal tubular member 22, or to the inner tubular member 27 (see embodiments of FIGS. 8 and 11). Although illustrated as a single layer in FIG. 1, the inner tubular member 27 may alternatively comprise a multilayered tubular member, which in one embodiment has an outer layer formed of the second polymeric material (e.g., nylon or PEBAX).

Support mandrel 36 within the inflation lumen 20 extends from the proximal end 12 of the catheter shaft 11 to the distal end 24 of the proximal tubular member 22 in the embodiment of FIG. 1. The support mandrel 36 is formed of a material selected from the group consisting of metals such as stainless steel and nickel titanium alloy, and high modulus polymers such as PEEK and nylon, and reinforced composites thereof, and is preferably formed of stainless steel. The support mandrel 36 has a distal section extending within the polymeric reinforcing member 32 adjacent to the inner surface of the polymeric reinforcing member 32, in contact with or alternatively, spaced from the inner surface of the polymeric reinforcing member. The support mandrel 36 may be bonded to the polymeric reinforcing member 32 or the proximal tubular member 22 along all or only part of its length, or alternatively it may be free-floating within the proximal tubular member and/or the polymeric reinforcing member. In the embodiment of FIG. 1, the support mandrel 36 is not in contact with the proximal tubular member 22 or with the polymeric reinforcing member 32 along the length of the support mandrel 36. Preferably the mandrel is not bonded to the polymeric reinforcing member 32. Typically, the polymeric material of the tubular members 22, 26, and 27 at the rapid exchange junction, or a separate polymeric member added therebetween, flows as the tubular members are fused together during catheter assembly, filling space therebetween as filler 42 (see FIG. 3). In one embodiment, the support mandrel 36 distal end is embedded therein. Thus, in an alternative embodiment (not shown) in which the support mandrel 36 extends beyond the distal end of the proximal tubular member 22 and the polymeric reinforcing member 32, the distal end of the support mandrel 36 is embedded within shaft polymeric material or filler material 42 between the tubular members 22, 27.

Figure 4:
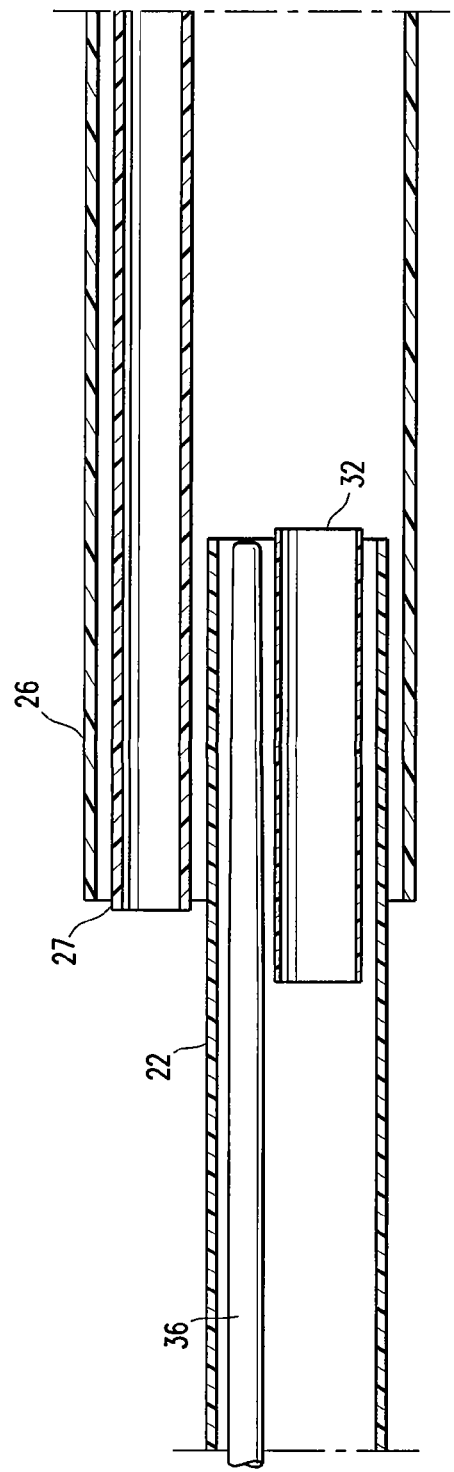
FIG. 4 is longitudinal cross section of an alternative rapid exchange junction which embodies features of the invention, prior to fusing of the tubular members together to form the junction during catheter assembly, having a polymeric reinforcing tube in the inflation lumen in the distal end of the proximal tubular member, with a support mandrel having a distal section extending along an outer surface of the polymeric reinforcing tube.

FIGS. 4 and 5 illustrate an alternative rapid exchange junction embodying features of the invention, in which the support mandrel 36 extends within the proximal tubular member 22 and adjacent to the outer surface of the polymeric reinforcing member 32 in the proximal tubular member 22. As best illustrated in FIGS. 6 and 7, showing transverse cross sectional views of the catheter of FIG. 5, taken along lines 6-6 and 7-7, respectively, the support mandrel extends in the proximal tubular member 22 from the proximal end to the distal end thereof. FIG. 4 illustrates the rapid exchange junction of FIG. 5, before the tubular members 22, 26 and 27 are fused together during catheter assembly. The catheter of FIG. 5 is assembled as outlined above for the embodiment of FIG. 1, except that an outer surface of the polymeric reinforcing member 32 is first bonded to an outer surface of the support mandrel 36 by adhesive bonding, or by fusion bonding to an outer bondable layer of the polymeric reinforcing member 32. Assembly rods (not shown) are placed within the lumens of the inner tubular member 27 and the proximal tubular member 22/polymeric reinforcing member 32 to keep the lumens open during the application of heat and pressure to fuse the tubular members 22, 26 and 27 together. The proximal tubular member 22 is then positioned around the support mandrel 36/polymeric reinforcing member 32 assembly, and, with an inflation lumen shaping assembly rod positioned in the polymeric reinforcing member and an assembly rod in the inner tubular member, shrink tubing around the outer tubular member 26 is heated to fuse the tubular members 22, 26 and 27 together and form the rapid exchange junction illustrated in FIG. 5.

Figure 8:
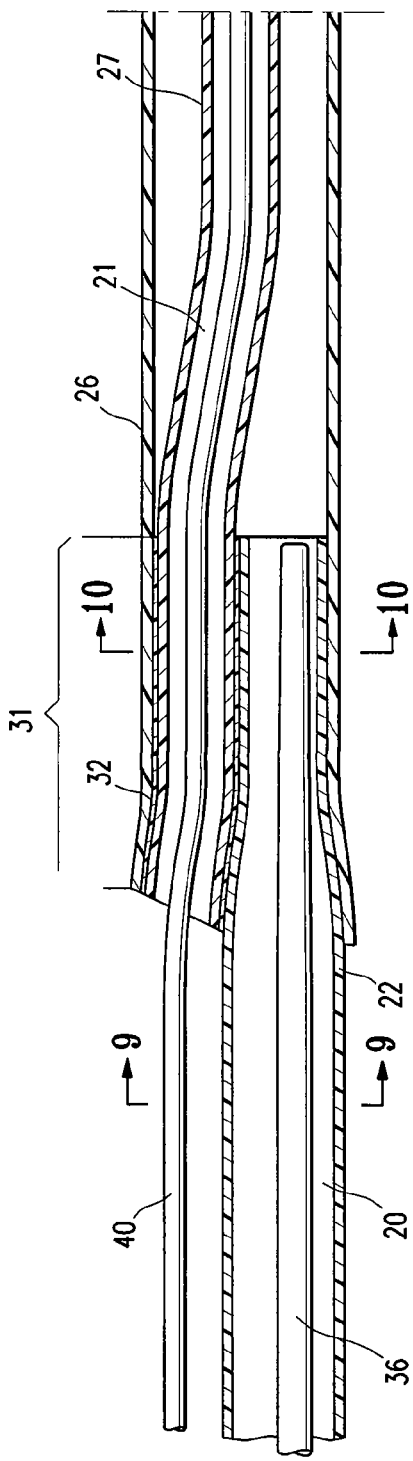
FIG. 8 is longitudinal cross section of an alternative rapid exchange junction which embodies features of the invention, having the polymeric reinforcing tube on an outer surface of the proximal portion of the inner tubular member, with a support mandrel in the inflation lumen in the proximal tubular member.
Figure 10:
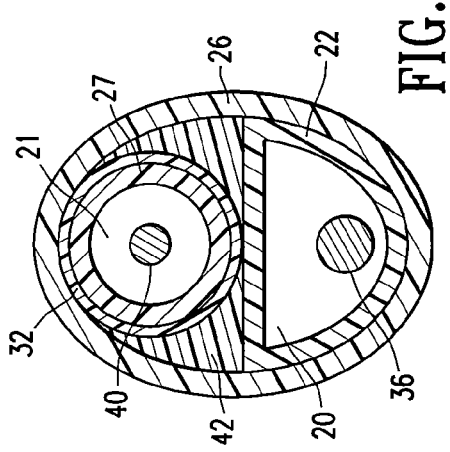
FIG. 10 is a transverse cross sectional view of the catheter shown in FIG. 8, taken along lines 10-10.
Figure 9:
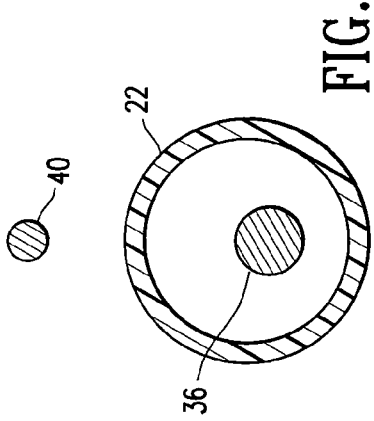
FIG. 9 is a transverse cross sectional view of the catheter shown in FIG. 8, taken along lines 9-9.

FIG. 8 illustrates an alternative rapid exchange junction embodying features of the invention, in which the polymeric reinforcing member 32 is on an outer surface of the proximal portion 31 of the inner tubular member 27. Support mandrel 36 extends within the proximal tubular member 22 from the proximal end to the distal end thereof. FIGS. 9 and 10 illustrate transverse cross sectional views of the catheter of FIG. 8, taken along lines 9-9, and 10-10, respectively. As best illustrated in FIG. 10, the distal end of the inflation lumen defined by the distal portion 25 of the proximal tubular member 22 is D-shaped. The D-shaped lumen section results from the shape of the assembly rod positioned in the proximal tubular member 22 during fusion of the tubular members. In alternative embodiments, the inflation lumen 20 may have a circular or oval shape. In the embodiment of FIG. 8, the polymeric reinforcing member 32 has a length approximately equal to the length of the proximal portion 31 of the inner tubular member 27 which is in a side-by-side relationship with the distal portion of the proximal tubular member 22. Alternatively, the distal end of the polymeric reinforcing member 32 may be located distal to the distal end of the proximal portion 31 of the inner tubular member 27. Polymeric material or filler 42 (see FIG. 10) typically fills the space within the outer tubular member 26 at the rapid exchange junction, between the outer tubular member 26 and the inner tubular member 27/proximal tubular member 22.

Figure 11:
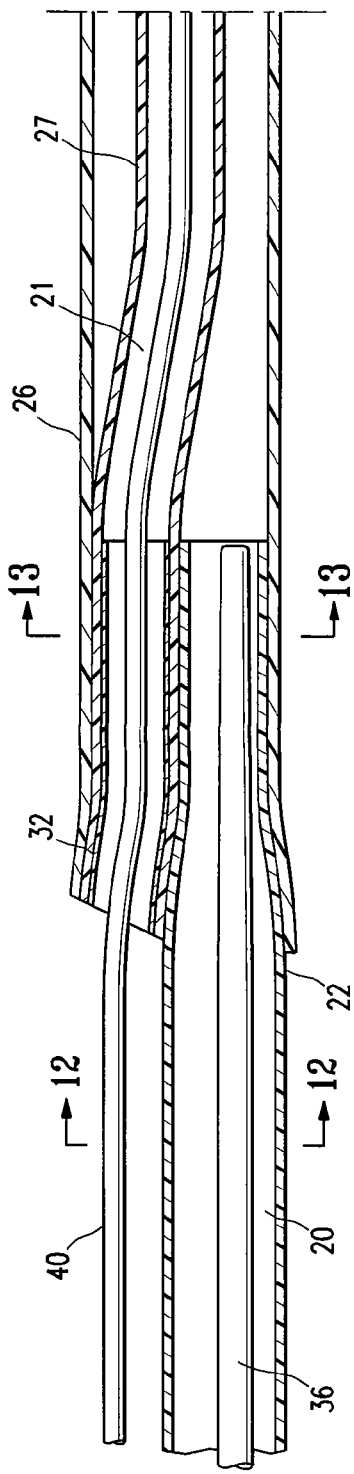
FIG. 11 is longitudinal cross section of an alternative rapid exchange junction which embodies features of the invention, having the polymeric reinforcing tube on an inner surface of the proximal portion of the inner tubular member, with a support mandrel in the inflation lumen in the proximal tubular member.
Figure 13:
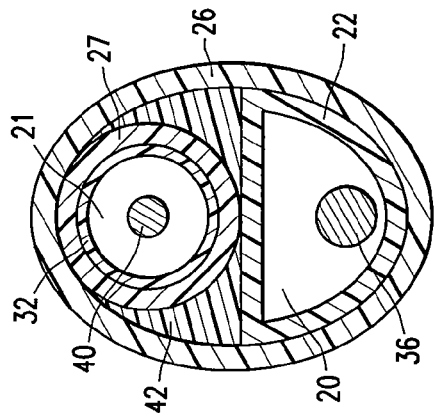
FIG. 13 is a transverse cross sectional view of the catheter shown in FIG. 11, taken along lines 13-13.
Figure 12:
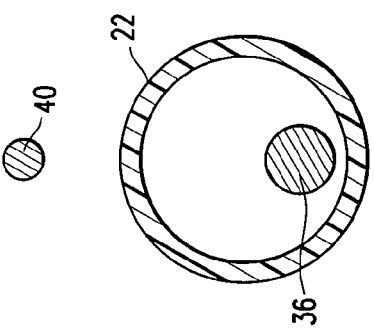
FIG. 12 is a transverse cross sectional view of the catheter shown in FIG. 11, taken along lines 12-12.

FIG. 11 illustrates an alternative rapid exchange junction embodying features of the invention, in which the polymeric reinforcing member 32 is on an inner surface of the proximal portion 31 of the inner tubular member 27. Support mandrel 36 extends within the proximal tubular member 22 from the proximal end to the distal end thereof. FIGS. 12 and 13 illustrate transverse cross sectional views of the catheter of FIG. 11, taken along lines 12-12, and 13-13, respectively.

In the illustrated embodiments, the proximal tubular member 22 is a single tubular member. In an alternative embodiment (not shown), the proximal tubular member 22 comprises a first tube, and a second tube distal to the first tube and having a proximal end bonded to a distal end of a first tube and forming the distal portion of the proximal tubular member 22. Thus, the proximal tubular member second tube forms a midshaft section, between the proximal first tube and the distal shaft section. The proximal tubular member first tube is typically formed of a material selected from the group consisting of a metal such as stainless steel, and a high modulus polymer such as PEEK or nylon, and in a presently preferred embodiment, the second tube is formed at least in part of the second polymeric material (e.g., nylon or PEBAX), typically adhesively bonded to the first tube.

The proximal tubular member 22, inner tubular member 27, and outer tubular member 26 of the catheters of the invention may be formed by conventional techniques, e.g. extruding, from materials already found useful in intravascular catheters such a polyethylene, polyamide, polyesters and composite materials. The use of the support mandrel 36 allows the use of otherwise soft materials, such as polyamide block copolymers, co-polyesters, nylon and polyurethanes, which are compatible with materials used to form dilatation balloons. This facilitates the bonding of the outer 26 and inner 27 tubular members to the balloon 14 by conventional techniques, such as laser bonding. The catheter components can be bonded together by heat fusion, adhesive, or by other conventional means. The polymeric reinforcing member 32 may be adhesively bonded, fusion bonded, or friction fit around or within the inner tubular member or the proximal tubular member, and is preferably secured thereto by ultraviolet curing adhesive such as is available from Loctite Corporation.

Figure 14:
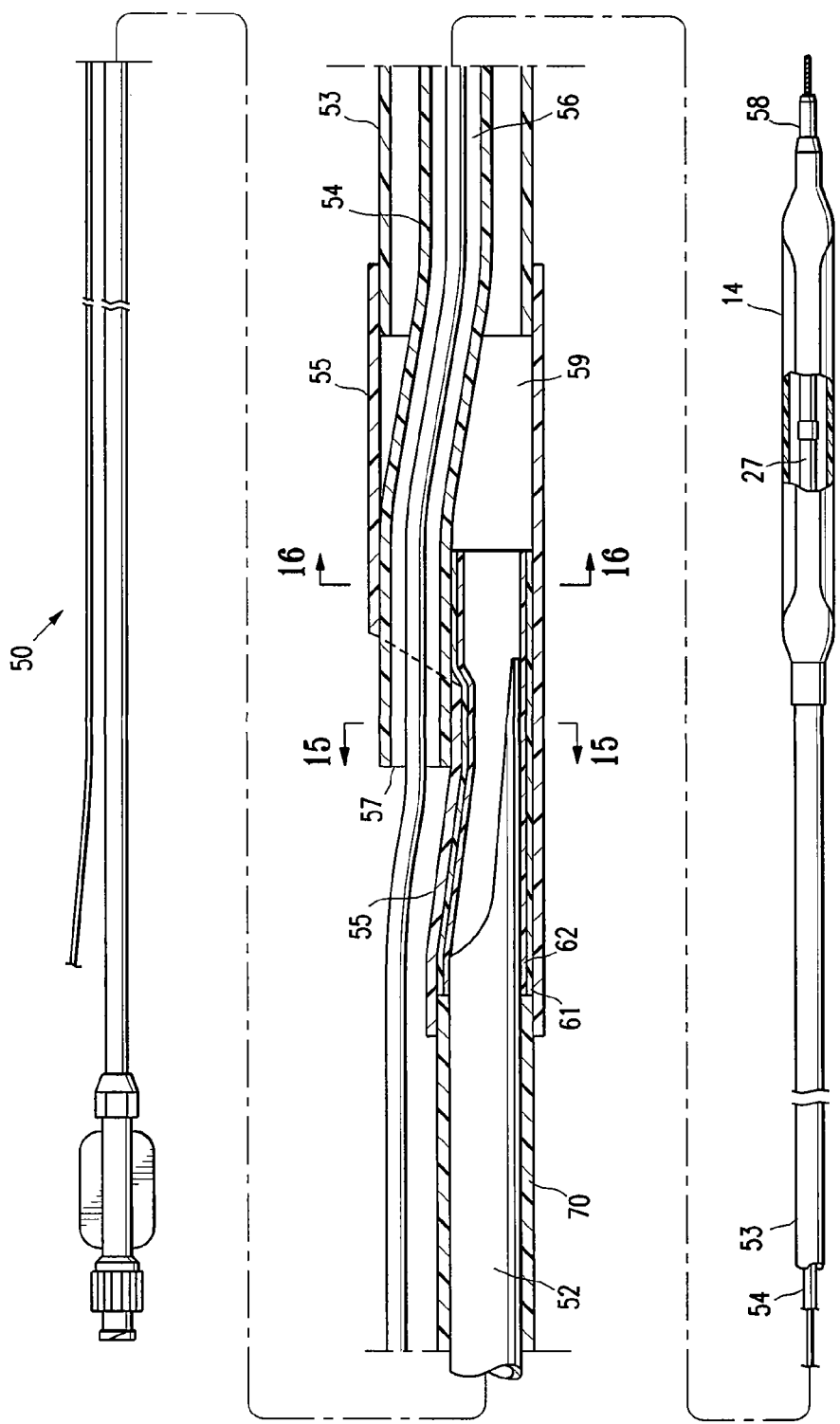
FIG. 14 illustrates an alternative aspect of the invention, directed to a balloon catheter having a multilayered sleeve at the rapid exchange intermediate section.

FIG. 14 illustrates an alternative embodiment of the invention, directed to a balloon catheter 50 having a multilayered sleeve 51 at the rapid exchange intermediate section. Catheter 50 has a proximal shaft section comprising a proximal tubular member 52, a distal shaft section comprising a distal outer tubular member 53 and a distal section of an inner tubular member 54, and an intermediate rapid exchange section therebetween. In the embodiment illustrated in FIG. 14, the intermediate section is formed by a mid-shaft outer tubular member 55 having a proximal end secured to a distal end of the proximal tubular member 52, and a distal end secured to a proximal end of the distal outer tubular member 53. In alternative embodiment, a separate mid-shaft outer tubular member is not provided, and the intermediate rapid-exchange section is formed at least in part by the proximal tubular member 52 and/or the distal outer tubular member 53. The intermediate section further comprises a proximal section of the inner tubular member 54 located within the mid-shaft outer tubular member 55, having the guidewire lumen 56 and a proximal end at a guidewire proximal port 57 in communication with a guidewire distal port 58 at the catheter distal end. The inner tubular member 54 has a proximal end portion 60 extending through a sidewall of the mid-shaft outer tubular member 55, so that the proximal end portion 60 has an outer surface extending along an outer surface of a portion of the mid-shaft outer tubular member 55. The inflation lumen 59 extends within the proximal tubular member 52, the mid-shaft outer tubular member 55, and the distal outer tubular member 53 to the interior of balloon 14 on the distal shaft section. Specifically, in the illustrated embodiment, a portion of the inflation lumen 59 within the intermediate shaft section is formed by the multilayered sleeve 51 and by the space between the inner tubular member 54 and the mid-shaft outer tubular member 55. Similarly, the inflation lumen within the distal shaft section is formed by the annular space between the inner tubular member 54 and the distal outer tubular member 56.

The multilayered sleeve 51 within the mid-shaft outer tubular member 55 has a proximal end on a distal end of the proximal tubular member 52, and extends distally from the distal end of the proximal tubular member 52 in a side-by-side relation to the proximal end portion 60 of the inner tubular member 54. A portion of the mid-shaft outer tubular member 55 separates the inflation lumen 59 from the guidewire lumen 56 at a proximal-most end of the inner tubular member 54. The nature of the polymers forming the multilayered sleeve is such, as discussed in more detail below, that the sleeve 51 is preferably a relatively short tubular member with a proximal end on the distal end of the proximal tubular member 52, and a distal end a relatively short distance distal to the proximal guidewire port 57 within the intermediate shaft section. In the illustrated embodiment, the proximal tubular member 52 has a polymeric jacket 70 thereon with a distal end proximal to the multilayered sleeve 51.

The multilayered sleeve 51 has coextensive outer and inner layers, the outer layer 61 being secured to an inner surface of the mid-shaft outer tubular member 55 and the inner layer 62 being secured to an inner surface of the outer layer 61. The multilayered sleeve 51 is preferably formed by coextruding the layers 61, 62 to form a coextruded tubular member.

The mid-shaft outer tubular member 55 is formed of a first polymeric material, the sleeve outer layer 61 is formed of a second polymeric material different than the first polymeric material, and the sleeve inner layer 62 is formed of a third polymeric material which is different than the second polymeric material and which may be the same as or different than the first polymeric material. The second polymeric material (forming sleeve outer layer 61) has a melting temperature or glass transition temperature significantly lower (i.e., at least about 20° C. lower) than that of the third polymeric material (forming sleeve inner layer 62) so that during formation of the intermediate shaft section by melt bonding of the inner tubular member 54 to the mid-shaft outer tubular member 55 at a relatively low temperature the multilayered sleeve outer layer 61 is melted and/or flows to form filler around the inflation lumen 59 at the guidewire proximal port 57, and the multilayered sleeve inner layer 62 retains a wall integrity around the inflation lumen 59. Typically, the second polymeric material melting temperature or glass transition temperature is also significantly lower than the first polymeric material (forming mid-shaft outer tubular member 55), so that the mid-shaft outer tubular member 55 retains a wall integrity around the inflation lumen 59 at the elevated temperature used during melt bonding of the intermediate shaft section tubular members.

Thus, the multilayered sleeve 51 facilitates heat sealing of the tubular members to form the rapid exchange intermediate section at a temperature significantly lower than (e.g., at least about 20° F. lower than) an elevated temperature required for a corresponding intermediate section having a single layered sleeve 51 formed of only the third polymeric material (i.e., just layer 62, without layer 61). As a result, as the inner member 54 is compressed against the sleeve 51 during the heat sealing (with mandrels in the guidewire lumen and inflation lumen to keep the lumens open during the heat sealing), thinning of the inner layer 62 is prevented or inhibited due to lower heat sealing temperature.

A variety of suitable materials can be used to form the multilayered sleeve. Typically, the outer layer 61 is formed of a polymer coextrudable with the polymeric material forming the inner layer 62, and having a melting temperature or glass transition temperature which is at least about 20° C. lower than a melting temperature/glass transition temperature of the inner layer 62 polymeric material. Additionally, the outer layer 61 polymeric material is preferably highly bondable to the adjacent polymeric materials. The outer layer 61 is fully encased by surrounding layers of polymeric material and therefore does not define an exposed outer or inner surface of the catheter shaft. As a result, the polymeric material forming the outer layer 61 need not be a lubricious material, and can be selected based on its melting point or glass transition temperature and its bondability. In one embodiment, the polymeric material forming the outer layer is a relatively nonlubricious material such as PRIMACOR which is highly bondable to the adjacent polymers.

The inner layer 62 can be formed of a variety of suitable materials which are sufficiently melt bondable to adjacent polymeric materials, including polyamides such as Nylon 12 and Nylon 11, and PEBAX (polyether block amide).

In a presently preferred embodiment, the multilayered sleeve 51 consists of tubing having outer layer 61 of a low melting modified polyolefin such as PRIMACOR (ethylene acrylic acid functionalized polyolefin), and an inner layer 62 of Nylon 12 or Nylon 11. PRIMACOR is relatively low melting, and is highly melt bondable to adjacent polymeric materials such as Nylon and HDPE, and is relatively nonlubricious. PRIMACOR has a melting temperature of about 203° F. (95° C.) and Nylon 12 has a melting temperature of about 340° F. (171° C.). Therefore, even at a relatively low heat sealing temperature of about 400° F. (204° C.) or below, the low melting outer layer 61 of the multilayered sleeve 51 melts and flows sufficiently to form filler material around the inflation lumen (i.e., polymeric material which flows into otherwise weakened wall portions formed as the polymeric tubular members are caused to thin as the tubular members are pressed together during heat bonding), while the Nylon 12 of the inner layer 62 maintains much of its wall thickness to maintain its wall integrity around the inflation lumen. In the absence of the low melting outer layer 62, a significantly higher temperature of at least about 420° F. (215° C.) to about 440° F. (227° C.) would be required to melt and flow a sleeve (located within the mid-shaft outer tubular member 55 in place of the multilayered sleeve 51) formed of a single layer of Nylon 12, sufficiently to form the filler at the intermediate section. However, at that significantly higher heat sealing temperature, the proximal end of the inner tubular member 54 is forced into the melted and flowing polymeric materials of the mid-shaft outer tubular member and the sleeve, resulting in an intermediate section prone to flexural failure and causing leaks or separation of the tubular members with propagation of cracks along the sleeve. As a result, the configuration of catheter 50 which facilitates use of the relatively low heat sealing temperature during assembly of the intermediate section, while still providing a filler material which was caused to melt and flow sufficiently to form filler around the inflation lumen, provides a catheter having an improved intermediate rapid exchange section which avoids leaks or separation of the tubular members at the high inflation pressures used for an angioplasty or stent deployment procedure.

Thus, the heat sealing temperature used during formation of the intermediate section, and the polymeric materials forming the low melting outer layer 61 and the inner layer 62 of the multilayered sleeve 51 are selected to allow for formation of an intermediate section which is not prone to flexural failure. In a presently preferred embodiment, the heat sealing temperature used during formation of the intermediate section is at least about 110° F. to about 220° F. (40° C. to 100° C.) greater than the melting temperature of the sleeve outer layer 62, but less than or not more than about 50° F. to about 95° F. (10° C. to 35° C.) greater than the melting temperature of the sleeve inner layer 61. In the embodiment having a PRIMACOR outer layer 62 and a Nylon 12 inner layer 61, the heat sealing temperature is preferably about 390° F. to about 400° F. (199° C. to 205° C.). The heat sealing temperature is the temperature applied to an outer surface of the intermediate section by an external heating source such as a heating nozzle or an oven. The inner layer 62 of the sleeve 51 typically reaches an elevated temperature which is somewhat lower than the heat sealing temperature, due to the insulative properties of the surrounding polymers which insulate the inner layer somewhat during the heat sealing. Similarly, the outer layer 61 of the multilayered sleeve 51 is insulated somewhat by the surrounding polymer layers including the section of the mid-shaft outer tubular member 55 surrounding the multilayered sleeve and extending between the inflation lumen and guidewire lumen at the proximal portion of the inner tubular member 54. However, the outer layer 61 is formed of a polymer having a sufficiently low melting temperature that the outer layer 61 melts and flows to form filler material during heat sealing as discussed above.

Figure 15:
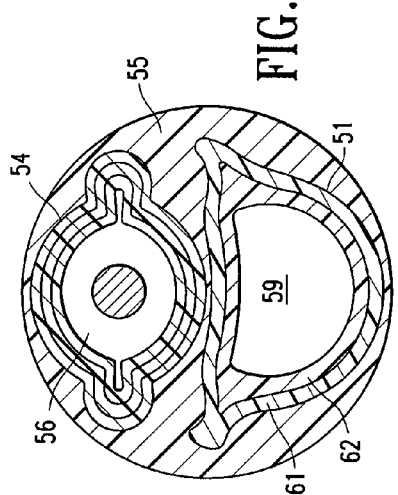
FIGS. 15 and 16 are transverse cross sectional views of the catheter shown in FIG. 14, taken along lines 15-15 and 16-16, respectively.
Figure 16:
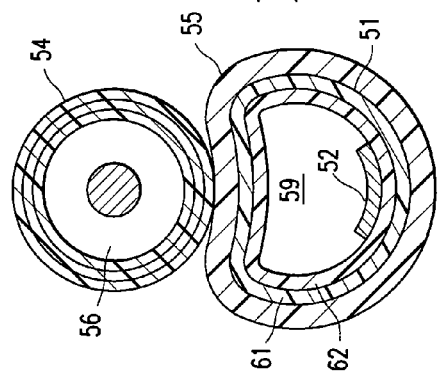

FIGS. 15 and 16 illustrate transverse cross sectional views of the catheter of FIG. 14, taken along lines 15-15 and 16-16, respectively. The sleeve outer layer 61 is illustrated as substantially retaining its generally annular transverse cross sectional shape in FIGS. 15 and 16. However, it should be understood that sections of the outer layer 61 will likely have an unpredictably irregular transverse cross sectional shape as a result of the low melting material of the outer layer 61 melting and flowing to fill in any weakened areas during formation of the rapid exchange intermediate section, as discussed above.

Figure 17:
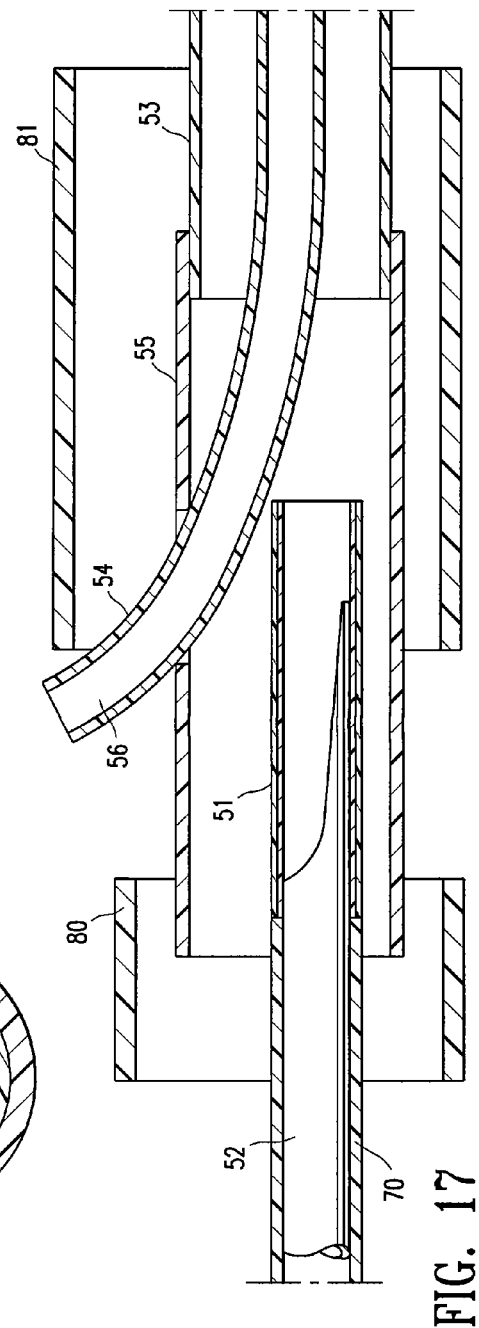
FIG. 17 illustrates the balloon catheter of FIG. 14, during formation of the rapid exchange intermediate section.

FIG. 17 illustrates the catheter of FIG. 14 during formation of the rapid exchange intermediate section. The inner tubular member 54 is positioned within the outer tubular members, with the proximal end portion of the inner tubular member 54 extending through the opening in the sidewall of the intermediate outer tubular member 55. The tubular members are illustrated in FIG. 17 prior to being heated and pressed together such that the proximal end portion of the inner tubular member forces the intermediate outer tubular member 55 against the multilayered sleeve 51. Heat shrink tubes 80 and 81 positioned around the shaft will radially shrink when heated, to press the tubular members together. The heat shrink tubes 80, 81 are then removed and discarded after the formation of the rapid exchange intermediate section is completed. Although not illustrated, mandrels would be present in the guidewire and inflation lumens in FIG. 17, to prevent the lumens from collapsing during bonding of the tubular members.

In the embodiment illustrated in FIGS. 15 and 16 the inner tubular member 54 is a trilayer multilayered tubular member (the inner tubular member is shown as a single layer in FIGS. 14 and 17 for ease of illustration). In one embodiment, the multilayered inner tubular member 54 has an inner layer which is compatible with and fusion bondable to the second polymeric material but which is not compatible with the third polymeric material. Thus, during formation of the rapid exchange junction, if the outer layers of the multilayered inner tubular member 54 flow and thin such that the inner layer of the inner tubular member 54 is exposed, the compatibility of the inner tubular member inner layer and the outer layer 61 of the multilayered sleeve 51 will prevent leaks or separation of parts at the rapid exchange junction during use of the catheter. For example, in one embodiment, the inner layer of the inner tubular member 54 is HDPE. HDPE does bond to PRIMACOR, but does not adhere well to Nylon, and as a result, the outer layer 61 of the multilayered sleeve 51 prevents or inhibits failure at the rapid exchange junction.

The catheter shaft will generally have the dimensions of conventional dilatation or stent delivery catheters. The length of the catheter 10, 50, measured from the distal end of the adapter 30 to the distal end of the catheter is about 90 to about 150 cm, typically about 137 cm. The proximal tubular member 22, 52 of the proximal shaft section 18 has a length of about 110 to about 120 cm, typically about 114 cm, an outer diameter (OD) of about 0.6 to about 1.3 mm, and an inner diameter (ID) of about 0.5 to about 1.1 mm. The outer tubular member 26, 53 of the distal shaft section 19 has a length of about 25 to about 35 cm, typically about 27 cm, an OD of about 0.76 to about 1.3 mm, and an ID of about 0.71 to about 1.2 mm. The inner tubular member 27, 54 of the distal shaft section 19 has a length of about 25 to about 35 cm, typically about 29 cm, an OD of about 0.5 to about 0.63 mm, and an ID of about 0.38 to about 0.5 mm. The inner and outer tubular members 27/26 may taper in the distal section to a smaller OD or ID. The diameter of support mandrel 36 may be adjusted as desired to achieve the desired handling characteristics, but generally should be about 0.005 to about 0.015 inch. The support mandrel 36 length is generally about 110 to about 125 cm.

The balloon 14 may be formed of a variety of suitable compliant, semi- or non-compliant, or hybrid compliant materials depending on the use of the catheter, e.g., dilatation, stent delivery, etc. The length of the balloon 14 is typically about 10 to 50 mm, more specifically about 18 to 40 mm. In an expanded state, the balloon diameter is typically about 1.5 to about 5 mm, more specifically about 1.5 to about 4 mm. The wall thickness will vary depending on the burst pressure requirements and hoop strength of the balloon material.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A method of making a balloon catheter, comprising:
    a) assembling a catheter shaft having a proximal tubular member, an outer tubular member formed of a first polymeric material distal to the proximal tubular member, a multilayered sleeve within the outer tubular member, and an inner tubular member which is within the outer tubular member and which has a proximal end portion extending out from the outer tubular member so that the proximal end portion of the inner tubular member has an outer surface extending along an outer surface of a portion of the outer tubular member, the multilayered sleeve having an outer layer formed of a second polymeric material and an inner layer formed of a third polymeric material, the second polymeric material having a melting temperature or glass transition temperature significantly lower than a melting temperature or glass transition temperature of the first polymeric material and the third polymeric material;
    b) heating and thermally fusing the inner tubular member to the outer tubular member at a heat sealing temperature which is sufficiently greater than the melting temperature or glass transition temperature of the second polymeric material so that the second polymeric material melts and/or flows to form filler around the inflation lumen, and which is sufficiently low so that the multilayered sleeve inner layer and the outer tubular member retain wall integrity around the inflation lumen; and
    c) bonding a balloon to a distal end section of the shaft so that the balloon has an interior in fluid communication with a lumen in the outer tubular member.

* * * * *